United States Patent [19]

White

[11] 4,278,439
[45] Jul. 14, 1981

[54] SENSITIZERS FOR PEROXIDATIVE ACTIVITY TESTS

[75] Inventor: William I. White, Elkhart, Ind.

[73] Assignee: Miles Laboratories, Inc., Elkhart, Ind.

[21] Appl. No.: 104,086

[22] Filed: Dec. 17, 1979

[51] Int. Cl.³ .................... C09K 3/00; G01N 33/48; G01N 31/22
[52] U.S. Cl. .................... 23/230 B; 23/901; 23/913; 23/931; 252/408; 422/55; 422/56; 435/28
[58] Field of Search .................... 23/230 B, 931, 913, 23/901; 252/408; 422/55, 56; 435/28

[56] References Cited

U.S. PATENT DOCUMENTS

| | | | |
|---|---|---|---|
| 3,012,976 | 12/1961 | Adams, Jr. et al. | 252/408 |
| 3,290,117 | 12/1966 | Adams, Jr. et al. | 252/408 |
| 3,853,472 | 12/1974 | Rittersdorf et al. | 252/408 |
| 3,917,452 | 11/1975 | Rittersdorf et al. | 252/408 |
| 3,947,377 | 3/1976 | Werner et al. | 252/408 |
| 3,975,161 | 8/1976 | Svoboda et al. | 23/230 B |
| 3,986,833 | 10/1976 | Mast et al. | 252/408 |
| 4,017,261 | 4/1977 | Svoboda et al. | 252/408 |
| 4,063,894 | 12/1977 | Ogawa et al. | 23/230 B |
| 4,071,321 | 1/1978 | Lam | 252/408 |
| 4,148,611 | 4/1979 | Nand et al. | 252/408 |

FOREIGN PATENT DOCUMENTS 52-17897  2/1977  Japan .................... 252/408

*Primary Examiner*—Teddy S. Gron
*Attorney, Agent, or Firm*—Charles J. Herron

[57] ABSTRACT

Improved test compositions, devices and methods for the detecting of peroxidatively active substances are provided. The test compositions include an indicator capable of being oxidized in the presence of peroxidatively active substances to provide a color change, an oxidizing agent effective to oxidize said indicator, and a sensitizing agent. The sensitizing agent comprises a compound selected from the class of compounds of the general formula:

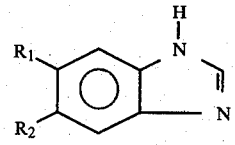

wherein $R_1$ and $R_2$ are independently selected from hydrogen and $C_1$–$C_4$ alkyl. Preferred compounds are benzimidazole and 5,6-dimethylbenzimidazole.

7 Claims, No Drawings

SENSITIZERS FOR PEROXIDATIVE ACTIVITY TESTS

BACKGROUND OF THE INVENTION

1. Field of the Invention

The present invention relates generally to the field of diagnostic tests and, more particularly, to those tests useful in qualitative and quantitative determination of peroxidatively active substances.

2. Description of the Prior Art

The detection of small amounts of peroxidatively active substances, such as occult blood, hemoglobin, myoglobin, leukocytes, bacteria, or other peroxidatively active analytes, in body fluids and in body excreta has long been recognized as an invaluable aid to the medical practitioner in the diagnosis of many abnormal conditions.

Various procedures, compositions and devices are described in the literature for the detection of occult peroxidatively active substances. For example, Kamlet in U.S. Pat. No. 2,290,436; Nicholls and Fonner in U.S. Pat. No. 2,799,660; Fonner in U.S. Pat. No. 2,838,377; and Adams and Peterson in U.S. Pat. Nos. 3,012,976, 3,092,463, and 3,092,464, all assigned to the instant assignee, illustrate several test compositions which have been supplied to meet the need for a simple, reliable test for occult blood. These test compositions are based on the peroxidative or catalytic activity of the prosthetic groups present in blood. See also Schwartz, Zeitschrift für gerichtlich Medizin (Journal of Forensic Medicine) 12: 1928.

It has been determined by Adams et al., in U.S. Pat. No. 3,290,117 that the sensitivity of these occult blood test compositions can be markedly improved and potentiated by the addition of quinoline or certain quinoline derivatives such as quinine. With the addition of these quinoline derivatives to the prior art occult blood compositions it is possible to detect 5 to 50 red blood cells (RBC)/microliter ($\mu$l) of sample which corresponds to a blood dilution as low as 1:1,000,000. Use of the acid addition salts or adducts of quinoline and its derivatives as potentiating agents is disclosed by Mast et al., in U.S. Pat. No. 3,986,833. Another approach, disclosed in U.S. Pat. No. 3,853,472, reports the use of fused polycyclic derivatives of quinoline, such as benzoquinolines and pyridoquinolines, as potentiating or activating agents with similar sensitivities. In U.S. Pat. No. 3,975,161 Svoboda et al., disclose the use of isoquinolines as potentiators.

Compounds other than those in the quinoline family have been found effective as well. In U.S. Pat. No. 3,917,452 Ritterdorf et al., disclose the use of vinyl pyridine compounds for use as sensitizers. In U.S. Pat. No. 4,063,894 Ogawa et al., disclose the use of substituted thiazole compounds for this purpose.

SUMMARY OF THE INVENTION

In accordance with the present invention, improved test compositions, devices and methods for the detecting of peroxidatively active substances are provided. The test compositions include an indicator capable of being oxidized in the presence of peroxidatively active substances to provide a color change, an oxidizing agent effective to oxidize said indicator, and a sensitizing agent. The sensitizing agent comprises a compound selected from the class of compounds of the general formula:

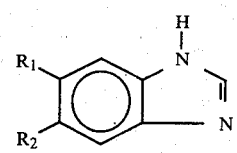

wherein $R_1$ and $R_2$ are independently selected from hydrogen and $C_1$-$C_4$ alkyl. Preferred compounds are benzimidazole and 5,6-dimethylbenzimidazole.

DESCRIPTION OF THE PREFERRED EMBODIMENTS

Although specific terms are used for clarity, these terms refer only to the embodiments selected for illustration, and are not intended to limit the scope of the invention.

The test compositions, which are improved by incorporation of the sensitizers described above, further contain at least an indicator and an oxidizing agent and may be prepared in a tablet form or incorporated with a carrier such as an absorbent matrix. Suitable indicators are capable of being oxidized in the presence of a peroxidatively active substance to provide a color change and include well known materials such as 3,3',5,5'-tetramethylbenzidine, o-tolidine, o-toluidine, p-toluidine, o-phenylenediamine, N,N'-dimethyl-p-phenylenediamine, N,N'-diethyl-p-phenylenediamine, benzidine, p-anisidine, dianisidine, o-cresol, m-cresol, p-cresol, alpha-naphthol, beta-naphthol, catechol, guaiacol, pyrogallol or those of the heterocyclic azine series for example bis-(N-ethyl-quinol-2-one)-azine or (N-methylbenzothiazol-2-one)-(1-ethyl-3-phenyl-5-methtriazol-2-one)-azine. As oxidizing agents there can be used, for example, cumene hydroperoxide, diisopropylbenzene hydroperoxide, paramenthane hydroperoxide, 2,5-dimethylhexane-2,5-dihydroperoxide and other well known oxidizing agents effective to oxidize the indicators.

In a preferred embodiment, the improved test compositions of this invention are incorporated on or with a carrier and utilized as a dip and read test device. The test device may be prepared by various well known methods which include impregnating an absorbent carrier material with a solution or solutions of the test composition and thereafter drying the impregnated matrix, thus adhesively incorporating within the matrix a finely divided, intimate mixture of the ingredients. The concentration range of sensitizing agent which can be used for impregnation solutions is generally from about 0.05 gram (g)/100 ml to about 1.0 g/100 ml and, preferably, from about 0.1 g/100 ml to about 0.5 g/100 ml. The term carrier refers to matrices which are insoluble in and maintain their structural integrity when exposed to physiological or other liquids to be tested. Suitable matrices which may be used include paper, cellulose, wood, synthetic resin fleeces, glass fiber, nonwoven and woven fabrics, various organic polymers, such as polypropylene, and other organic materials well known as film formers to those skilled in the art. Alternatively, the carrier may take the form of a pressed or molded tablet containing conventional carrier material. For convenience, the carrier can be suitably attached to an insoluble support or handle member which can be made from polystyrene.

The test device is advantageously used by momentarily dipping it in a test sample or by otherwise introducing a test sample into the carrier matrix, whereby a detectable color change results when the peroxidatively active analyte is present. The volumetric capacity of the carrier serves to limit the amount of sample absorbed thereby and to which the test composition incorporated therewith is exposed. Any excess sample can be removed by washing or blotting the carrier to thereby limit the amount of sample tested to the volume thereof which has actually entered the carrier matrix. The test device can be used in the same way when samples of plasma, serum or other body fluids are tested.

Test devices in the form of treated carrier matrices are often stored for considerable periods of time before use, and it is therefore desirable that the reagents chosen are not easily auto-oxidizable in air. Advisably, the test devices should be protected from exposure to light and in some cases it is desirable to keep them sealed in a moisture repellent package which is opened only for removal of one or more test devices shortly before use.

Reflectance readings of color produced by reaction with the peroxidatively active analyte present in the sample can be obtained from commercially available spectrophotometers such as Beckman DK-2 Spectrophotometer, Beckman Instruments, Inc., Fullerton, California or Spectrocolorimeter SCF-1, Israel Electrooptical Industry Ltd. (distributed in the U.S. by Broomer Research Corporation, Plainwell, Long Island, N.Y.).

The following example illustrates preferred embodiments of the invention.

EXAMPLE I

This example reports tests performed to compare the sensitizing agents according to the invention with a known sensitizing agent, 6-methoxy quinoline.

Four impregnation solutions were prepared as follows: 1. The following compounds were added to 41.67 milliliters (ml) of distilled water in the following order. Each ingredient was dissolved before the next was added.

sodium citrate—1.78 grams (g)
citric acid—2.31 g.
triethanolamine borate—5.56 g.
versene—0.055 g.
methyl sulfone—5.56 g.
sodium lauryl sulfate—0.833 g.

Then, 41.67 ml N,N-dimethylformamide was added to this solution and then the following compounds were added:

6-methoxy quinoline—0.333 g.
cumene hydroperoxide—1.667 g.
o-tolidine—0.444 g.

2. Same, except no 6-methoxy quinoline
3. Substitute 0.124 g. benzimidazole for 6-methoxy quinoline
4. Substitute 0.153 g. 5,6-dimethylbenzimidazole for 6-methoxy quinoline.

A 10 inches×4 inches piece of Eaton & Dikeman No. 237 paper was impregnated to saturation with the first solution and dried 11 minutes at 95°–97° C. Identical pieces of paper were then each impregnated with one of the remaining solutions. They were then cut into pieces 0.2 inch×0.2 inch and attached to plastic handles.

Solutions of hemoglobin were prepared and the devices prepared above were tested both fresh and after stress storage of 1 week at 60° C. The lowest detectable levels of hemoglobin in urine are reported as milligrams (mg)/deciliter (dl) in Table I.

TABLE I
Lowest Detectable Levels of Hemoglobin in Urine

| Sensitizer | Fresh (mg/dl) | 1 wk 60° C. (mg/dl) |
|---|---|---|
| 1. 6-methoxy quinoline | 0.016 | 0.064 |
| 2. none | 0.322 | >0.805 |
| 3. benzimidazole | 0.064 | 0.322 |
| 4. 5,6-dimethylbenzimidazole | 0.032 | 0.161 |

These results show that the compounds used in accordance with the invention are effective as sensitizers in the detection of peroxidatively active substances, such as occult blood.

Although the invention has been described with a certain degree of particularily, numerous changes may be resorted to without departing from the scope of the invention.

I claim:

1. A test composition for detection of peroxidatively active substances in body fluids, body excreta, and the like, including an indicator capable of being oxidized in the presence of a peroxidatively active substance to provide a color change, an oxidizing agent effective to oxidize said indicator, and an effective amount of a sensitizing agent selected from the class of compounds having the formula:

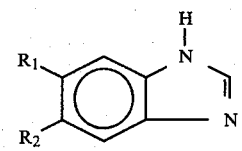

wherein $R_1$ and $R_2$ are independently selected from hydrogen and $C_1$-$C_4$ alkyl.

2. The composition of claim 1 wherein said sensitizing agent is benzimidazole.

3. The composition of claim 1 wherein said sensitizing agent is 5,6-dimethylbenzimidazole.

4. A test device for detection of peroxidatively active substances in body fluids, body excreta, and the like, which comprises a carrier incorporated with the composition of claim 1.

5. A test device for detection of peroxidatively active substances which comprises a carrier incorporated with the composition of claim 2.

6. A test device for detection of peroxidatively active substances in body fluids, body excreta, and the like, which comprises a carrier incorporated with the composition of claim 3.

7. A method for the determination of peroxidatively active substances in body fluids, body excreta, and the like, which comprises contacting test sample with the composition of claim 1 and observing any resultant color change.

* * * * *

UNITED STATES PATENT AND TRADEMARK OFFICE
CERTIFICATE OF CORRECTION

PATENT NO. : 4,278,439

DATED : July 14, 1981

INVENTOR(S) : William I. White

It is certified that error appears in the above-identified patent and that said Letters Patent are hereby corrected as shown below:

In claim 5, line 2, after "substances" insert --- in body fluids, body excreta and the like ---.

Signed and Sealed this

Sixth Day of October 1981

[SEAL]

Attest:

Attesting Officer

GERALD J. MOSSINGHOFF

Commissioner of Patents and Trademarks